(12) United States Patent
Anke et al.

(10) Patent No.: US 6,384,186 B2
(45) Date of Patent: May 7, 2002

(54) CYCLIC DODECAPEPTIDE AND PROCESS FOR THE PREPARATION THEREOF

(75) Inventors: Heidrun Anke, Kaiserslautern; Winfried Etzel, Leichlingen; Wolfgang Gau, Wuppertal; Rüdiger Hain, Langenfeld; Michael Kilian, Leverkusen; Anke Mayer, Landau, all of (DE); Olov Sterner, Malmö (SE)

(73) Assignee: Bayer Aktiengesellschaft, Leverkusen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/077,489

(22) PCT Filed: Nov. 25, 1996

(86) PCT No.: PCT/EP96/05199

§ 371 Date: May 29, 1998

§ 102(e) Date: May 29, 1998

(87) PCT Pub. No.: WO97/20857

PCT Pub. Date: Jun. 12, 1997

(30) Foreign Application Priority Data

Dec. 6, 1995 (DE) .......................... 195 45 463

(51) Int. Cl.⁷ .............................. C07K 7/08; C07K 7/64
(52) U.S. Cl. ........................ 530/317; 530/329; 424/405; 435/69.1; 435/254.1; 504/117
(58) Field of Search ...................... 514/9, 16; 530/317, 530/329; 424/405; 426/37; 504/117; 435/69.1, 254.1

(56) References Cited

PUBLICATIONS

File Caplus on STN, AN No. 1997:86488. Meyer et al. Screening of Higher Fungi for the Production of Nematicidal Compounds Using Melaoidogyne Incognita (Kofoid & White) Chitwood as Test Organism, Meded. Fac. Landbouwkd. Toegepaste Biol. Wet. (Univ. Gen.*

File Scisearch on STN, AN No. 91:233894. Arnone et al. 'Secondary Mold Metabolites .31. Isolation and Structure Elucidation of Illudins–A and Illudins–B, and Illudanlenol, New Sesquiterpenoids Form Clitocybe–Illudens,' Journal of the Chemical Society–P.*

* cited by examiner

Primary Examiner—Christopher S. F. Low
Assistant Examiner—Anish Gupta
(74) Attorney, Agent, or Firm—Norris McLaughlin & Marcus

(57) ABSTRACT

The present invention relates to a novel organochemical compound, referred to as omphalotin for short, a process for its preparation by an essentially microbiological route and its use as microbicide and pesticide, preferably for controlling animal pests, harmful fungi and bacteria.

8 Claims, 3 Drawing Sheets

| H atom | δ/ppm | Multiplicity | rel.No.H | H atom | &/ppm | Multiplicity | rel.No.H |
|---|---|---|---|---|---|---|---|
| 58 | 10.73 | D | 1 | 39a | 1.05 | M | 1 |
| 8 | 8.89 | D | 1 | 46b | 0.94 | M | 1 |
| 25 | 8.27 | D | 1 | 35 | 0.91 | D | 3 |
| 16 | 7.90 | D | 1 | 36 | 0.88 | S | 3 |
| 4 | 7.66 | D | 1 | 47 | 0.83 | T | 3 |
| 1 | 7.26 | M | 1 | 57 | 0.80 | D | 3 |
| 5 | 7.03 | S | 1 | 42 | 0.80 | D | 3 |
| 2 | 7.01 | M | 1 | 39b | 0.78 | M | 1 |
| 3 | 6.92 | M | 1 | 45 | 0.79 | D | 3 |
| 22 | 5.09 | D | 1 | 53 | 0.77 | D | 3 |
| 12 | 5.03 | D | 1 | 49 | 0.75 | D | 3 |
| 14 | 5.02 | D | 1 | 51 | 0.74 | T | 3 |
| 7 | 5.00 | M | 1 | 43 | 0.73 | D | 3 |
| 18 | 4.92 | D | 1 | 38 | 0.71 | D | 3 |
| 29 | 4.88 | D | 1 | 54 | 0.67 | D | 3 |
| 9a | 4.77 | D | 1 | 56 | 0.65 | D | 3 |
| 26a | 4.59 | D | 1 | 40 | 0.64 | T | 3 |
| 27 | 2.81 | S | 3 | 32 | 0.60 | D | 3 |
| 30 | 2.76 | S | 3 | 33 | 0.21 | D | 3 |
| 11 | 2.72 | S | 3 | 24 | 4.48 | T | 1 |
| 13 | 2.71 | S | 3 | 15 | 4.46 | T | 1 |
| 19 | 2.59 | S | 3 | 20a | 4.30 | D | 1 |
| 41 | 2.22 | M | 1 | 28 | 3.84 | D | 1 |
| 52 | 2.19 | M | 1 | 9b | 3.66 | D | 1 |
| 55 | 2.11 | M | 1 | 20b | 3.46 | M | 1 |
| 48 | 2.06 | M | 1 | 26b | 3.30 | D | 1 |
| 37 | 2.02 | M | 1 | 6a | 3.17 | DD | 1 |
| 44 | 1.98 | M | 1 | 23 | 3.01 | S | 3 |
| 31 | 1.95 | M | 1 | 17 | 2.97 | S | 3 |
| 34 | 1.90 | M | 1 | 21 | 2.93 | S | 3 |
| 50a | 1.53 | M | 1 | 10 | 2.89 | S | 3 |
| 46a | 1.18 | M | 1 | 6b | 2.88 | DD | 1 |
| 50b | 1.07 | M | 1 | | | | |

FIG. 1

| C atom | δ/ppm | Multiplicity | rel. No.C | C atom | δ/ppm | Multiplicity | rel. No.C |
|---|---|---|---|---|---|---|---|
| 39 | 23.1 | T | 1 | 34 | 29.9 | D | 1 |
| 11 | 28.9 | Q | 1 | 21 | 36.3 | Q | 1 |
| 47 | 11.0 | Q | 1 | 9 | 49.0 | T | 1 |
| 40 | 10.4 | Q | 1 | 7 | 49.3 | D | 1 |
| 49 | 14.1 | Q | 1 | 26 | 50.1 | T | 1 |
| 51 | 9.9 | Q | 1 | 20 | 50.7 | T | 1 |
| 56 | 17.0 | Q | 1 | 15 | 52.9 | D | 1 |
| 53 | 19.1 | Q | 1 | 24 | 53.8 | D | 1 |
| 33 | 17.3 | Q | 1 | 22 | 55.3 | D | 1 |
| 54 | 17.5 | Q | 1 | 12 | 57.0 | D | 1 |
| 38 | 15.5 | Q | 1 | 18 | 57.5 | D | 1 |
| 45 | 16.3 | Q | 1 | 14 | 57.7 | D | 1 |
| 32 | 18.4 | Q | 1 | 29 | 58.5 | D | 1 |
| 57 | 19.5 | Q | 1 | 28 | 63.9 | D | 1 |
| 43 | 17.6 | Q | 1 | XV | 109.9 | S | 1 |
| 42 | 19.5 | Q | 1 | 1 | 110.9 | D | 1 |
| 19 | 29.1 | Q | 1 | 3 | 117.9 | D | 1 |
| 50 | 25.0 | Q | 3 | 4 | 118.1 | D | 1 |
| 52 | 26.1 | D | 3 | 2 | 120.5 | D | 1 |
| 35 | 18.7 | Q | 3 | 5 | 123.5 | D | 1 |
| 36 | 18.7 | Q | 3 | XIV | 127.5 | S | 1 |
| 41 | 26.1 | D | 3 | XIII | 135.9 | S | 1 |
| 48 | 34.1 | D | 1 | IX | 167.8 | S | 1 |
| 37 | 34.1 | D | 1 | VI | 167.9 | S | 1 |
| 46 | 22.9 | T | 1 | XII | 167.9 | S | 1 |
| 13 | 29.0 | Q | 1 | VII | 168.0 | S | 1 |
| 17 | 29.8 | Q | 1 | VIII | 168.4 | S | 1 |
| 31 | 27.0 | D | 1 | II | 168.4 | S | 1 |
| 27 | 36.0 | Q | 1 | IV | 168.8 | S | 1 |
| 30 | 28.6 | Q | 1 | V | 168.8 | S | 1 |
| 23 | 30.5 | Q | 1 | XI | 169.6 | S | 1 |
| 10 | 36.0 | Q | 1 | I | 170.9 | S | 1 |
| 44 | 32.0 | D | 1 | X | 172.0 | S | 1 |
| 6 | 28.0 | T | 1 | III | 172.3 | S | 1 |
| 55 | 25.7 | D | 1 | | | | |

FIG. 2 a) Appearance: white powder b) Solubility: readily soluble in methanol, acetone and 2-propanol, less readily soluble in ethyl acetate and hardly soluble in cyclohexane and t-butyl methyl ether c) Molecular Weight: 1317 d) Empirical Formula (elemental analysis): $C_{69} H_{11} N_{13} O_{12}$

5) Spectra: The data of the $^1H$ NMR spectra are shown in Tables 1 and 2 of the description

SEQUENCE LISTING

<160> NUMBER OF SEQ ID NOS: 1

<210> SEQ ID NO 1
<211> LENGTH: 12

```
<212> TYPE: PRT
<213> ORGANISM: Unknown Organism
<220> FEATURE:
<223> OTHER INFORMATION: Description of Unknown Organism:A microorganism
      from the class of Basidiomycetes, from the genera
      Omphalotus and Lampteromyces
<220> FEATURE:
<221> NAME/KEY: MOD_RES
<222> LOCATION: (2)
<223> OTHER INFORMATION: METHYLATION
<220> FEATURE:
<221> NAME/KEY: MOD_RES
<222> LOCATION: (3)..(8)
<223> OTHER INFORMATION: METHYLATION
<220> FEATURE:
<221> NAME/KEY: MOD_RES
<222> LOCATION: (10)..(11)
<223> OTHER INFORMATION: METHYLATION

<400> SEQUENCE: 1

Trp Val Ile Val Val Gly Val Ile Gly Val Ile Gly
  1               5                  10
```

CYCLIC DODECAPEPTIDE AND PROCESS FOR THE PREPARATION THEREOF

The present invention relates to a novel organochemical compound, hereinafter referred to as omphalotin, a process for its preparation by an essentially microbiological route and its use as microbicide and pesticide, preferably for controlling animal pests, harmful fungi and bacteria.

The novel omphalotin has been found and, based on the present spectroscopic and other analytical data, the following formula (I) is proposed:

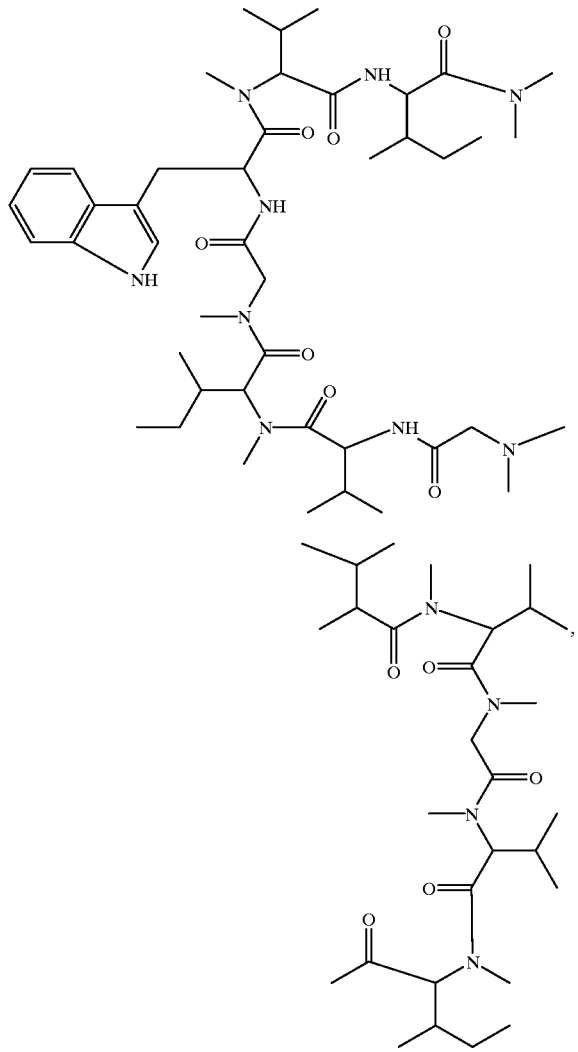

(I)

where —(terminal) represents —CH₃,

represents

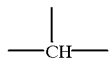

or (terminal) represents

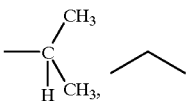

represents —CH₂—,

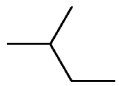

represents

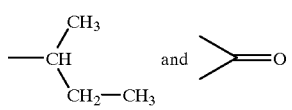

represents

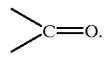

Furthermore, it has been found that the novel omphalotin can be employed for controlling pests and parasites in plants and warm-blooded animals. In particular, it has high activity against nematodes and arthropods (like insects and arachnids), and against microbial pests, in particular against fungi and bacteria. Owing to these properties, the novel compound and compositions comprising this compound can be employed particularly advantageously in crop protection, in the protection of stored products, in the hygiene sector and in animal breeding and animal husbandry.

The novel compound of the formula (I) is obtained by cultivating suitable microorganisms from the class of the Basidiomycetes, preferably from the genera Omphalotus and Lampteromyces, particularly preferably Omphalotus, in a customary manner in a cultured medium containing assimilable carbon and nitrogen sources and mineral salts, under aerobic conditions, and isolating the desired compound by customary methods.

Knowing the properties of the novel compound according to the invention, it is possible in an easy and quick manner to select the appropriate microorganism strains which produce the omphalotin according to the invention by routine processes, with the aid of customary chromatographic, spectroscopic, microbiological (for example inhibition zone test) and/or biological methods (for example by determining the activity against nematodes or insects).

For the microbiological preparation of the compound according to the invention, preference is given to using omphalotus strains, in particular Omphalotus olearius strains (synonym: Clitocybe illudens strains). Very particular preference is given to using the Omphalotus olearius strains No.

83 039, 90 173, 91 050, 92 095, 93 162 and 90 170 and those variants and mutants of these strains which have features which are essential for carrying out the present invention, or which have the same function.

BRIEF DESCRIPTION OF THE DRAWINGS

The invention will now be described in greater detail with reference to the drawings wherein:

FIG. 1 is a table indicating the $^1$H NMR spectra data for a compound according to the invention;

FIG. 2 is another table indicating the $^1$H NMR spectra data for a compound according to the invention.

Figure 3:
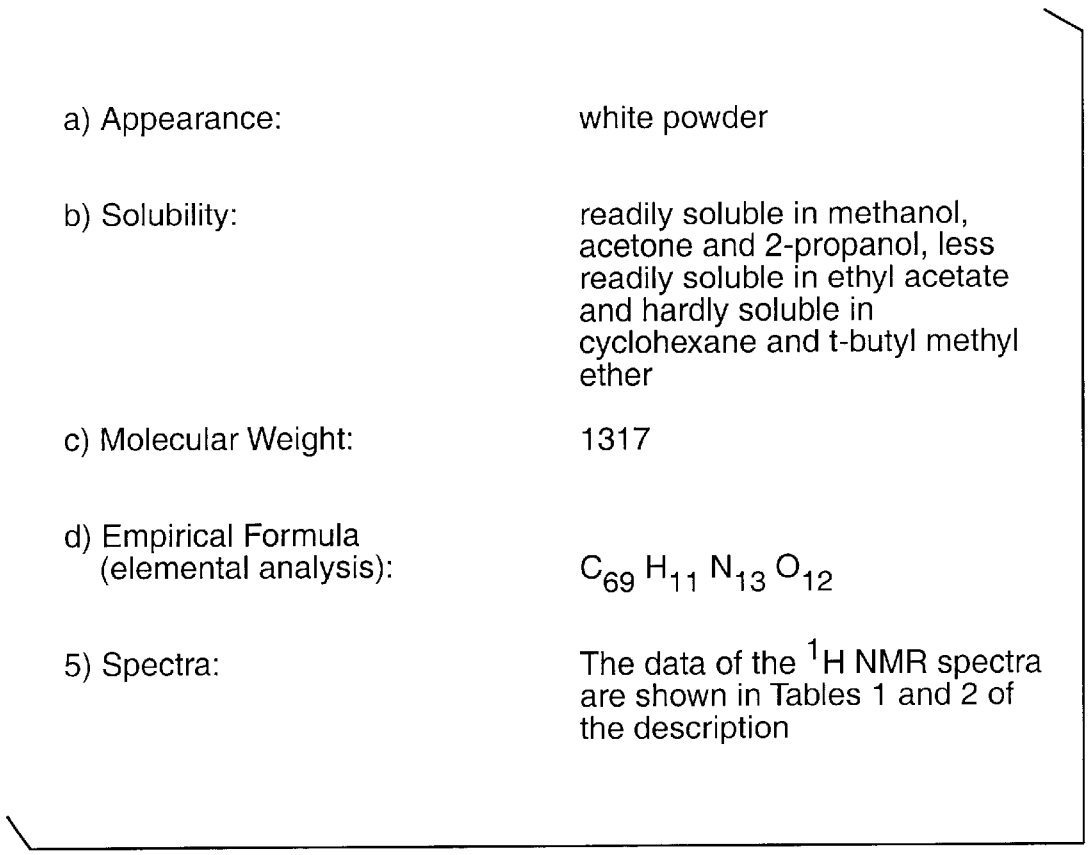
FIG. 3 is a table summarizing some physico-chemical data and spectra for a compound according to the invention.

The novel strains can be described as follows:

1. Comparison of the morphology of the mycel of various Omphalotus olearius strains on solid medium (M1)

| Fungus strain | Mycel consistency and colour |
| --- | --- |
| Omphalotus olearius 83 039 (DSM 9737) | The mycel which is white at the beginning of growth only changes colour to a pale yellow, in rare cases somewhat brownish. Secretions, as observed with the other strains, were not observed. |
| Omphalotus olearius 90 170 (DSM 9742) | The young mycel is white-fluffy, the older mycel changes colour to orange-black. In some cases droplets of brown colour are secreted. |
| Omphalotus olearius 90 173 (DSM 9738) | The young white mycel grows less dense and fluffy than 90 170. The older mycel is initially pale yellow and later changes colour to orange-black. In some cases, brown secretions are observed. |
| Omphalotus olearius 91 050 (DSM 9739) | Growth and mycel colour are similar to that of 90 170, however, the secretions of brown droplets are more numerous. |
| Omphalotus olearius 92 095 (DSM 9740) | The young white mycel changes colour to an intense orange, later slightly brownish. The secretion of brown droplets is very pronounced. The mycel does not turn black. |
| Omphalotus olearius 93 162 (DSM 9741) | Similar to 92 095, the young yellow mycel changes colour to an intense orange and likewise secretes many brown drops. |

2. Growth of various Omphalotus olearius strains at different temperatures in 1 l of a shaken culture M1 medium in a 2 l Erlenmeyer flask.

|  | Incubation temperature [° C.] | | |
| --- | --- | --- | --- |
| Fungus strain | 24 | 27 | 30 |
| Omphalotus olearius 83 039 (DSM 9737) | maximum growth rate | medium growth rate | strongly reduced growth |
| Omphalotus olearius 90 170 (DSM 9742) |  | Slightly less growth than at 30° C. | maximum growth rate |
| Omphalotus olearius 90 173 (DSM 9738) |  | Identical growth at all temperatures | |
| Omphalotus olearius 91 050 (DSM 9739) |  | Identical growth at all temperatures | |
| Omphalotus olearius 92 095 (DSM 9740) | medium growth rate | maximum growth rate | lowest growth rate |
| Omphalotus olearius 93 162 (DSM 9741) | maximum growth rate | maximum growth rate | lowest growth rate |

3. Form and size of the pellets of the various Omphalotus olearius strains at growth in liquid culture (M1)

| Fungus strain | Form and size of pellet |
| --- | --- |
| Omphalotus olearius 83 039 (DSM 9737) | The fungus forms firm pellets of a diameter of 0.5 to 1.5 cm |
| Omphalotus olearius 90 170 (DSM 9742) | The fungus grows in very small firm pellets having a diameter of about 0.5 cm |
| Omphalotus olearius 90 173 (DSM 9738) | The fungus grows with a similar pellet form and size as 90 170 |
| Omphalotus olearius 91 050 (DSM 9739) | The pellet size varies frequently but is generally slightly greater than for 90 170 (0.5 to 1.5 cm). The pellet is "frazzled". |
| Omphalotus olearius 92 095 (DSM 9740) | The fungus forms the largest pellets of a diameter of 1 to 2 cm and a "prickly" surface. |
| Omphalotus olearius 93 163 (DSM 9741) | The fungus forms pellets having a diameter of up to 1.5 cm and less firm, more "frazzled" structure. |

The abovementioned Omphalotus olearius strains are novel. They have been deposited at the Deutschen Sammlung von Mikroorganismen und Zellkullturen GmbH (DSM), Mascheroder Weg 1b, D 38124 Braunschweig, Federal Republic of Germany, in accordance with the provisions of the Treaty of Budapest on the international recognition of the deposition of microorganisms for the purpose of patent processes and have the following deposition numbers or entry numbers:

| Strain | Number and date of deposition | |
| --- | --- | --- |
| Omphalotus olearius No. 83 039 | DSM 9737 | 13.02.1995 |
| Omphalotus olearius No. 90 173 | DSM 9738 | 13.02.1995 |
| Omphalotus olearius No. 91 050 | DSM 9739 | 13.02.1995 |
| Omphalotus olearius No. 92 095 | DSM 9740 | 13.02.1995 |
| Omphalotus olearius No. 93 162 | DSM 9741 | 13.02.1995 |
| Omphalotus olearius No. 90 179 | DSM 9742 | 13.02.1995 |

The structure of the Omphalotus isolated from Omphalotus olearius was elucidated with the aid of $^1$H, $^{13}$C, COSY, NOESY, HMQC and HMBC NMR spectra, and an ESI MS spectrum. The molecular mass was determined to be 1318 Da. The NMR spectra were recorded using a solution of about 3 mg of the substance in $d_6$-DMSO. The $^1$H and $^{13}$C NMR spectra were recorded on a Bruker AMX400 machine, the 2-D spectra were recorded using a Bruker DMX-600. The individual amino acids were assigned with the aid of the COSY and the HMQC spectrum. With the aid of the COSY spectrum, the proton signals of the individual amino acids are assigned starting from the NH, or the α proton, by means of the H-H couplings. By using the HMQC spectrum, it is then possible to assign the carbon signals in a similar manner. The sequence of the amino acids was determined with the aid of the NOESY and the HMBC spectrum. In the NOESY spectrum, the spatial distance of the NH of an amino acid to the α proton(s) of the next amino acid is detected. In the HMBC spectrum, the α protons of two amino acids which are linked to each other are correlated to the same carbonyl carbon. The α protons also show two correlation peaks to carbonyl carbons: one peak by two-bond coupling to the carbonyl carbon of its own amino acid and one peak by three-bond coupling to the carbonyl carbon of the N-linked amino acid.

The following structure was determined:

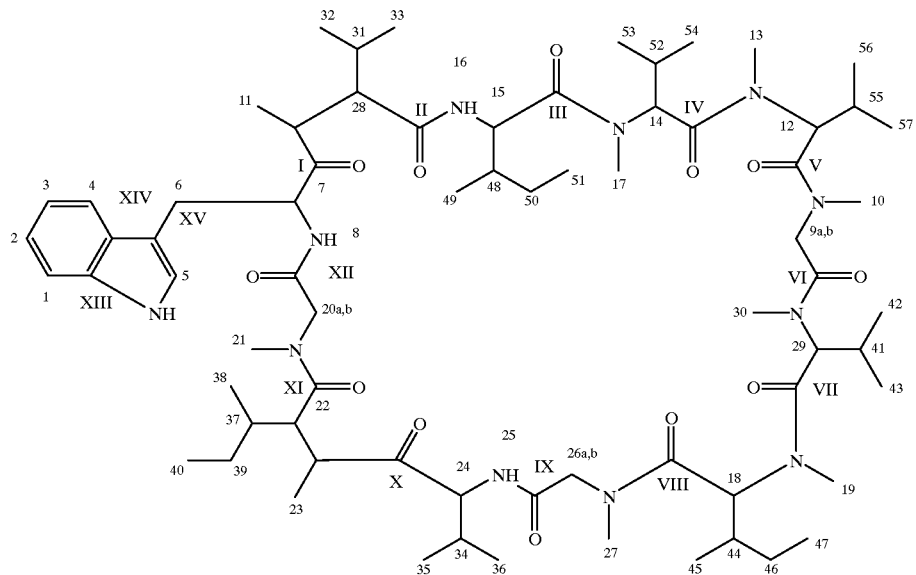

The $^1$H and $^{13}$C signals were assigned as shown in the two tables below:

TABLE 1

| H atom | δ/ppm | Multiplicity | rel. No. H |
|---|---|---|---|
| 58 | 10.73 | D | 1 |
| 8 | 8.89 | D | 1 |
| 25 | 8.27 | D | 1 |
| 16 | 7.90 | D | 1 |
| 4 | 7.66 | D | 1 |
| 1 | 7.26 | M | 1 |
| 5 | 7.03 | S | 1 |
| 2 | 7.01 | M | 1 |
| 3 | 6.92 | M | 1 |
| 22 | 5.09 | D | 1 |
| 12 | 5.03 | D | 1 |
| 14 | 5.02 | D | 1 |
| 7 | 5.00 | M | 1 |
| 18 | 4.92 | D | 1 |
| 29 | 4.88 | D | 1 |
| 9a | 4.77 | D | 1 |
| 26a | 4.59 | D | 1 |
| 27 | 2.81 | S | 3 |
| 30 | 2.76 | S | 3 |
| 11 | 2.72 | S | 3 |
| 13 | 2.71 | S | 3 |
| 19 | 2.59 | S | 3 |
| 41 | 2.22 | M | 1 |
| 52 | 2.19 | M | 1 |
| 55 | 2.11 | M | 1 |
| 48 | 2.06 | M | 1 |
| 37 | 2.02 | M | 1 |
| 44 | 1.98 | M | 1 |
| 31 | 1.95 | M | 1 |
| 34 | 1.90 | M | 1 |
| 50a | 1.53 | M | 1 |
| 46a | 1.18 | M | 1 |
| 50b | 1.07 | M | 1 |
| 39a | 1.05 | M | 1 |
| 46b | 0.94 | M | 1 |
| 35 | 0.91 | D | 3 |
| 36 | 0.88 | S | 3 |
| 47 | 0.83 | T | 3 |
| 57 | 0.80 | D | 3 |
| 42 | 0.80 | D | 3 |
| 39b | 0.78 | M | 1 |
| 45 | 0.79 | D | 3 |
| 53 | 0.77 | D | 3 |
| 49 | 0.75 | D | 3 |
| 51 | 0.74 | T | 3 |
| 43 | 0.73 | D | 3 |
| 38 | 0.71 | D | 3 |
| 54 | 0.67 | D | 3 |
| 56 | 0.65 | D | 3 |
| 40 | 0.64 | T | 3 |
| 32 | 0.60 | D | 3 |
| 33 | 0.21 | D | 3 |
| 24 | 4.48 | T | 1 |
| 15 | 4.46 | T | 1 |
| 20a | 4.30 | D | 1 |
| 28 | 3.84 | D | 1 |
| 9b | 3.66 | D | 1 |
| 20b | 3.46 | M | 1 |
| 26b | 3.30 | D | 1 |
| 6a | 3.17 | DD | 1 |
| 23 | 3.01 | S | 3 |

TABLE 1-continued

| H atom | δ/ppm | Multiplicity | rel. No. H |
|---|---|---|---|
| 17 | 2.97 | S | 3 |
| 21 | 2.93 | S | 3 |
| 10 | 2.89 | S | 3 |
| 6b | 2.88 | DD | 1 |

TABLE 2

| C atom | δ/ppm | Multiplicity | rel. No. H |
|---|---|---|---|
| 39 | 23.1 | T | 1 |
| 11 | 28.9 | Q | 1 |
| 47 | 11.0 | Q | 1 |
| 40 | 10.4 | Q | 1 |
| 49 | 14.1 | Q | 1 |
| 51 | 9.9 | Q | 1 |
| 56 | 17.0 | Q | 1 |
| 53 | 19.1 | Q | 1 |
| 33 | 17.3 | Q | 1 |
| 54 | 17.5 | Q | 1 |
| 38 | 15.5 | Q | 1 |
| 45 | 16.3 | Q | 1 |
| 32 | 18.4 | Q | 1 |
| 57 | 19.5 | Q | 1 |
| 43 | 17.6 | Q | 1 |
| 42 | 19.5 | Q | 1 |
| 19 | 29.1 | Q | 1 |
| 50 | 25.0 | Q | 3 |
| 52 | 26.1 | D | 3 |
| 35 | 18.7 | Q | 3 |
| 36 | 18.7 | Q | 3 |
| 41 | 26.1 | D | 3 |
| 48 | 34.1 | D | 1 |
| 37 | 34.1 | D | 1 |
| 46 | 22.9 | T | 1 |
| 13 | 29.0 | Q | 1 |
| 17 | 29.8 | Q | 1 |
| 31 | 27.0 | D | 1 |
| 27 | 36.0 | Q | 1 |
| 30 | 28.6 | Q | 1 |
| 23 | 30.5 | Q | 1 |
| 10 | 36.0 | Q | 1 |
| 44 | 32.0 | D | 1 |
| 6 | 28.0 | T | 1 |
| 55 | 25.7 | D | 1 |
| 34 | 29.9 | D | 1 |
| 21 | 36.3 | Q | 1 |
| 9 | 49.0 | T | 1 |
| 7 | 49.3 | D | 1 |
| 26 | 50.1 | T | 1 |
| 20 | 50.7 | T | 1 |
| 15 | 52.9 | D | 1 |
| 24 | 53.8 | D | 1 |
| 22 | 55.3 | D | 1 |
| 12 | 57.0 | D | 1 |
| 18 | 57.5 | D | 1 |
| 14 | 57.7 | D | 1 |
| 29 | 58.5 | D | 1 |
| 28 | 63.9 | D | 1 |
| XV | 109.9 | S | 1 |
| 1 | 110.9 | D | 1 |
| 3 | 117.9 | D | 1 |
| 4 | 118.1 | D | 1 |
| 2 | 120.5 | D | 1 |
| 5 | 123.5 | D | 1 |
| XIV | 127.5 | S | 1 |
| XIII | 135.9 | S | 1 |
| IX | 167.8 | S | 1 |
| VI | 167.9 | S | 1 |
| XII | 167.9 | S | 1 |
| VII | 168.0 | S | 1 |
| VIII | 168.4 | S | 1 |
| II | 168.4 | S | 1 |
| IV | 168.8 | S | 1 |
| V | 168.8 | S | 1 |

TABLE 2-continued

| C atom | δ/ppm | Multiplicity | rel. No. H |
|---|---|---|---|
| XI | 169.6 | S | 1 |
| I | 170.9 | S | 1 |
| X | 172.0 | S | 1 |
| III | 172.3 | S | 1 |

The structure of the novel compound according to the invention was determined by extensive analytical, in particular spectroscopic, studies. However, since errors in the interpretation of the analytical data of substances of complex structure cannot always be totally excluded, omphalotin is additionally described by some characteristic physicochemical data and spectra.

TABLE 3

| | |
|---|---|
| a) Appearance: | white powder |
| b) Solubility | readily soluble in methanol, acetone and 2-propanol, less readily soluble in ethyl acetate and hardly soluble in cyclohexane and t-butyl methyl ether |
| c) Molecular weight: | 1317 |
| d) Empirical formula (elemental analysis): | $C_{69}H_{115}N_{13}O_{12}$ |
| e) Spectra | The data of the $^1$H NMR spectra are shown in Tables 1 and 2 of the description. |

According to the invention, the novel omphalotin is produced by the fermentation of suitable strains of microorganisms from the class of the Basidiomycetes, in particular of the orders Omphalotus and Lampteromyces, preferably Omphalotus olearius (synonym: Clitocybe illudens) and very particularly preferably of the Omphalotus olearius strains 83 039 (DSM 9737), 90 173 (DSM 9738), 91 050 (DSM 9739), 92 095 (DSM 9740), 93 162 (DSM 9741) or 90 170 (DSM 9742) or by mutants or variants thereof.

The fermentation process according to the invention is carried out in a customary manner. It can be carried out with the aid of solid, semi-solid or liquid culture media. Preference is given to using aqueous-liquid culture media.

The culture media are inoculated by customary methods, for example using oblique tubes or flask cultures.

The cultivation is carried out under aerobic conditions and can be carried out according to customary methods, for example by using shaking cultures for example a shaking flask, by using air-agitated cultures or submersion cultures. Preference is given to carrying out the cultivation using the aerobic submersion process in aerated fermenters, for example in customary submersion fermentation tanks. The cultivation can be carried out continuously or batchwise. Preference is given to batchwise operation.

The cultivation can be carried out in all culture media which are known to be used for the cultivation of microorganisms of the class of the Basidiomycetes. The culture medium must contain one or more assimilable carbon sources and nitrogen sources and mineral salts, it being possible for these products to be present in the form of defined individual components, or else in the form of complex mixtures, as represented in particular by biological products of diverse origin. Suitable carbon sources are all customary carbon sources. Examples include carbohydrates, in particular polysaccharides, such as starch or dextrins, disaccharides, such as maltose or cane sugar, monosaccharides such as glucose or xylose, sugar alcohols such as mannitol or glycerol and naturally occurring mixtures such as malt extract, molasses or whey powder. Suitable nitrogen sources are all customary organic and inorganic nitrogen sources. Examples include proteins, protein hydrolysates, amino acids such as glutamic acid, aspartic acid, arginine, lysine, ornithine or serine, nucleoside bases such as cytosine or uracil and soya bean meal, cotton seed meal, lentil meal, pea meal, soluble and insoluble plant proteins, maize steep liquor, yeast extract, peptones and meat extract and also ammonium salts and nitrates, for example $NH_4Cl$, $(NH_4)_2SO_4$, $NaNO_3$ and $KNO_3$. The mineral salts which should be present in the culture medium generate, for example, the following ions:

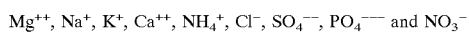

$Mg^{++}$, $Na^+$, $K^+$, $Ca^{++}$, $NH_4^+$, $Cl^-$, $SO_4^{--}$, $PO_4^{---}$ and $NO_3^-$ and ions of the customary trace elements, such as Cu, Fe, Mn, Mo, Zn, Co, Ni. If the carbon or nitrogen sources or the water used do not contain enough of these salts or trace elements it is useful to supplement the culture medium appropriately. The composition of the culture media can vary within wide ranges. The kind and the composition of the culture media will generally depend on which components are in each case available at particularly low cost. In general, the culture solutions contain preferably about 0.5 to 8%, in particular 0.6 to 6%, of carbon sources, preferably about 0.5 to 4%, in particular 0.5 to 2%, of nitrogen sources and preferably about 0.001 to 0.5%, in particular 0.003 to 0.3%, of mineral salts.

When carrying out the process, it may be advantageous to use only relatively low concentrations of the soluble culture solution components at the beginning of the cultivation, and to feed these components in the form of sterile, relatively concentrated solution to the culture broth by relatively frequent addition over the first 3 days of cultivation.

The pH of the growing cultures should preferably be maintained at between about 5 and about 10, in particular between 3.0 and 8.0. An unacceptably large decrease in pH into the acid range can be avoided by addition of an organic or inorganic base, preferably $CaCO_3$. As is customary in fermentation technology, it is also possible to carry out an automatic pH regulation where sterile organic or inorganic acid, for example $H_2SO_4$, or sterile base, for example NaOH, is injected into the culture broth in intervals.

It is useful to make sure that the microorganisms are in sufficient contact with oxygen and the nutrients. This can be ensured by customary methods such as shaking and stirring.

The cultivation temperature may be between about 15 and about 40° C., preferably between 20 and 35° C., particularly preferably, the temperature is between about 22 and 27° C. The duration of the cultivation can vary within wide limits, depending, for example, on the composition of the culture medium and the cultivation temperature. The particular optimum conditions can easily be determined by any person skilled in the art of microbiology.

It has been found that the amount of the compound according to the invention which becomes enriched in the cultivation broth generally reaches its maximum after about 1 to 10, preferably about 4 to 7, days after the beginning of the cultivation. The desired end product of fermentation can be determined with the aid of thin-layer-chromatographical studies, with the aid of HPLC and UV absorption spectra, in the plate diffusion test using a suitable fungus as test strain, or by the nematicidal or insecticidal activity.

As in all microbiological processes, extraneous infections of the culture media should be avoided. For this purpose, the usual precautions are taken, such as sterilization of the culture media, of the culture vessels and of the air required for aeration. For the sterilization of the equipment, it is for example possible to use both steam and dry sterilization, the temperatures preferably being at 100 to 140° C., in particular at 120 to 130° C.

If foam is formed in undesirable quantities during the cultivation, the customary chemical defoamers, for example liquid fats and oils, oil-water emulsions, paraffins, higher alcohols, such as octadecanol, silicone oils, polyoxyethylene or polyoxypropylene compounds (for example in amounts of up to about 1%) may be added. Foam may also be reduced or eliminated with the aid of the customary mechanical devices (which use, for example, centrifugal forces).

The compound according to the invention can be isolated by customary physico-chemical methods from the culture medium and from the biomass. The isolation may be carried out for example by the customary extraction processes, precipitation processes and/or chromatographic processes. The final purification of the isolated substance may also be carried out with the aid of the abovementioned methods. However, in many cases a final purification is not necessary, since minor impurities which may be present do not adversely affect the activity of the compound.

When carrying out the abovementioned isolation and purification methods, customary physico-chemical methods, for example measuring of a characteristic band in the spectrum or of the $R_f$ values, determination of the antimicrobial or of the nematicidal and insecticidal activity, etc., may be employed to find the fractions in which the compound according to the invention is present in the highest concentration or purity. These methods can also be employed to find suitable microorganisms by routine processes.

The isolation and purification of the compound according to the invention, for example in the case where a liquid aqueous culture medium is used, can be carried out as follows:

After it is enriched in the supernatant of the culture, culture filtrate and mycel are separated by customary methods (for example centrifugation).

The compound according to the invention can be isolated, and, if appropriate, purified, from the culture filtrate, preferably from the biomass, with the aid of customary extraction processes, precipitation processes and/or chromatographic processes. Chromatography can be carried out in the form of column chromatography.

Suitable for use as adsorbents are the customary inorganic or organic adsorbents, such as, for example, alumina, silica gel, magnesium silicate, activated charcoal, cellulose, cellulose derivatives, synthetic resins such as polyamides, for example acetylated polyamide, dextran gels or modified dextran gels. Suitable for use as eluents are all the different solvents or solvent mixtures in which the compound according to the invention is soluble. Preference is given to using water, ammonia solution, chloroform and methanol or mixtures thereof (for example mixtures of chloroform, methanol and aqueous $NH_3$ or methanol and water).

For the isolation of the compound according to the invention, preference is given to using chromatographic processes, for example non-specific adsorption on sorbents such as silica gel, ion exchange chromatography or gel diffusion chromatography. These are methods which are known from the purification of water-soluble charged natural compounds.

Furthermore, the countercurrent distribution (liquid-liquid distribution) methods may also be employed advantageously.

The compound according to the invention can be obtained from its solutions by customary methods, for example by the evaporation of the solvent, freeze-drying, etc.

In a preferred embodiment of the invention, the biomass (the mycel) is obtained by centrifugation of the fermentation material (culture broth and mycel) which is obtained by the aerobic cultivation of the strains at about 27° C.

The novel substance is preferably obtained by extraction of the biomass. It can also be isolated from the culture filtrate by adsorption on activated charcoal or on suitable resins. The most economical method has been proven to be the binding of the substance according to the invention to unspecific adsorber resins based on polystyrene (for example Amberlite XAD or Lewatit OC 1031). Desorption of the compounds according to the invention is carried out fractionally, by mixtures of water and organic solvents, in particular water/methanol. The fractions which show activity in the test against Meloidogyne incognita are concentrated under reduced pressure until the organic solvent has been completely removed and, if appropriate, lyophilized.

The lyophilized crude product is taken up in water and, after insoluble components have been separated off, purified further by customary chromatographic processes. Here, preference is given to renewed binding to absorber resins (for example Lewatit OC 1031), a further purification of the active fractions by chromatography (for example Sephadex LH 20). The novel substance is finally prepared in pure form by customary chromatographic methods, preferably by silica gel chromatography or preparative HPLC.

The compound according to the invention is suitable for controlling animal pests, in particular insects, arachnids and nematodes, encountered in agriculture, in forests, in the protection of stored products and of materials, and in the hygiene sector. It is preferably used as a crop protection agent. It is active against normally sensitive and resistant species and against all or some stages of development. The abovementioned pests include:

From the order of the Isopoda, for example, *Oniscus asellus, Armadillidium vulgare* and *Porcellio scaber*.

From the order of the Diplopoda, for example, *Blaniulus guttulatus*.

From the order of the Chilopoda, for example, *Geophilus carpophagus* and *Scutigera spec.*

From the order of the Symphyla, for example, *Scutigerella immaculata*.

From the order of the Thysanura, for example, *Lepisma saccharina*.

From the order of the Collembola, for example, *Onychiurus armatus*.

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria*.

From the order of the Dernaptera, for example, *Forficula auricularia*.

From the order of the Isoptera, for example, Reticulitermes spp.

From the order of the Anoplura, for example, *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci*.

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix,* Pemphigus spp., *Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Spodoptera litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica*.

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypodenna spp., Tabanus spp., Tannia spp., *Bibio hortulanus, Oscinella frit,* Phorbia spp., *Pegomyia hyoscyami, Ceratitis capitata, Dacus oleae* and *Tipula paludosa*.

From the order of the Siphonaptera, for example, *Xenopsylla cheopis* and Ceratophyllus spp.

From the order of the Arachnida, for example, *Scorpio maurus* and *Latrodectus mactans*.

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The phytoparasitic nematodes include, for example, Pratylenchus spp., *Radopholus similis, Ditylenchus dipsaci, Tylenchulus semipenetrans,* Heterodera spp., Globodera spp., Meloidogyne spp., Aphelenchoides spp., Longidorus spp., Xiphinema spp. and Trichodorus spp.

Microbial pests which can be controlled with the aid of the novel compound include in particular the phytopathogenic fungi:

Plasmodiophoromycetes, Oomycetes, Chytridiomycetes, Zygomycetes, Ascomycetes, Basidiomycetes and Deuteromycetes.

Phytopathogenic bacteria include in particular Pseudomonadaceae, Rhizobiaceae, Enterobacteriaceae, Corynebacteriaceae and Streptomycetaceae.

Some pathogens causing fungal and bacterial diseases which come under the generic names listed above are mentioned as examples, but not by way of limitation:

Xanthomonas species, such as, for example, *Xanthomonas campestris* pv. *oryzae*; Pseudomonas species, such as, for example, *Pseudomonas syringae* pv. *lachrymans*; Erwinia species, such as, for example, *Erwinia amylovora*; Pythium species, such as, for example, *Pythium ultimum*; Phytophora species, such as, for example, *Phytophthora infestans*;

Pseudoperonospora species, such as, for example, *Pseudoperonospora humuli* or *Pseudoperonospora cubense*; Plasmopara species, such as, for example, *Plasmopara viticola*; Peronospora species, such as, for example, *Peronospora pisi* or *P. brassicae;*

Erysiphe species, such as, for example, *Erysiphe graminis*; Sphaerotheca species, such as, for example, *Sphaerotheca fuliginea*; Podosphaera species, such as, for example, *Podosphaera leucotricha*; Venturia species, such as, for example, *Venturia inaequalis*; Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium); Uromyces species, such as, for example, *Uromyces appendiculatus*; Puccinia species, such as, for example, *Puccinia recondita*; Tilletia species, such as, for example, *Tilletia caries*; Ustilago species, such as, for example, *Ustilago nuda* or *Ustilago avenae*; Pellicularia species, such as, for example, *Pellicularia sasakii*; Pyricularia species, such as, for example, *Pyricularia oryzae*; Fusarium species, such as, for example, *Fusarium culmorum;*

Botrytis species, such as, for example, *Botrytis cinerea*; Septoria species, such as, for example, *Septoria nodorum; Leptosphaeria species, such as, for example, Leptosphaeria nodorum*; Cercospora species, such as, for example, *Cercospora canescens*; Alternaria species, such as, for example, *Alternaria brassicae*; and Pseudocercosporella species, such as, for example, *Pseudocercosporella herpotrichoides.* Furthermore, Helminthosporium carbonum may be mentioned.

The compound of the formula (I) according to the invention in particular has outstanding nematicidal activity, for example against *Meloidogyne incognita*.

It has systemic action and can also be applied via the leaves.

The active compound can be converted to the customary formulations, such as solutions, emulsions, wettable powders, suspensions, powders, dusting agents, pastes, soluble powders, granules, suspo-emulsion concentrates, natural and synthetic materials impregnated with active compound and very fine capsules in polymeric substances.

These formulations are produced in a known manner, for example by mixing the active compound with extenders, that is liquid solvents and/or solid carriers, if appropriate with the use of surfactants, that is emulsifiers and/or dispersants and/or foam-formers.

If the extender used is water, it is also possible to use for example organic solvents as auxiliary solvents. Suitable liquid solvents are essentially: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, for example mineral oil fractions, mineral and vegetable oils, alcohols, such as butanol or glycol and their ethers and esters, ketones, such as acetone, methyl ethyl ketone, methyl isobutyl ketone or cyclohexanone, strongly polar solvents, such as dimethylformamide and dimethyl sulphoxide and water.

Suitable solid carriers are:

for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks such as calcite, marble, pumice, sepiolite and dolomite, and synthetic granules of inorganic and organic meals, and granules of organic material such as sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysates; suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, and natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compound according to the invention can be present in its commercially available formulations and in the use forms, prepared from these formulations, as a mixture with other active compounds, such as insecticides, attractants, sterilizing agents, bactericides, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

Examples of particularly advantageous mixing components are the following:

Fungicides 2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)-benzamide; (E)-2-methoxyimino-N-methyl-2-(2-phenoxyphenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoxymino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cypro-conazole, cyprofuram, dichlorophen, diclobutrazol, diclofluanid, diclomezine, dicloran, diethofencarb, difenoconazole, dimethirimol, dimethomorph, diniconazole, dinocap, diphenylamine, dipyrithione, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, irninoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclofos-methyl, tolylfluanid, triadimefon, triadimenol, triazoxide, trichlamide, tricyclazole, tridemorph, triflumizole, triforine, triticonazole, validamycin A, vinclozolin, zineb, ziram.

Bactericides bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/Acaricides/Nematicides abamectin, AC 303 630, acephate, acrinathrin, alanycarb, aldicarb, alphamethrin, amitraz, avermectin, AZ 60541, azadirachtin, azinphos A, azinphos M, azocyclotin, Bacillus thuringiensis, bendiocarb, benfuracarb, bensultap, beta-cyfluthrin, bifenthrin, BPMC, brofenprox, bromophos A, bufencarb, buprofezin, butocarboxim, butylpyridaben, cadusafos, carbaryl, carbofuran, carbophenothion, carbosulfan, cartap, CGA 157419, CGA 184699, chloethocarb, chlorethoxyfos, chlorfenvinphos, chlorfluazuron, chlormiephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimfos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonofos, formothion, fosthiazate, fubfenprox, furathiocarb, HCH, heptenophos, hexaflumuron, hexythiazox, imidacloprid, iprobenfos, isazofos, isofenphos, isoprocarb, isoxathion, ivermectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemeton M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozine, pyrachlofos, pyridaphenthion, pyresmethrin, pyrethrum, pyridaben, pyrimidifen, pyriproxyfen, quinalphos, RH 5992, salithion, sebufos, silafluofen, sulfotep, sulprofos, tebufenozide, tebufenpyrad, tebupirimifos, teflubenzuron, tefluthrin, temephos, terbam, terbufos, tetrachlorvinphos, thiafenox, thiodicarb, thiofanox, thiomethon, thionazin, thuringiensin, tralomethrin, triarathene, triazophos, triazuron, trichlorfon, triflumuron, trimethacarb, vamidothion, XMC, xylylcarb, YI 5301/5302, zetamethrin.

A mixture with other known active compounds, such as herbicides, or with fertilizers and growth-regulators is also possible.

The active compound according to the invention can furthermore be present in its commercially available formulations and in the use forms, prepared from these formulations, as a mixture with synergists. Synergists are compounds which increase the action of the active compounds, without it being necessary for the synergist added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compound is employed in a customary manner appropriate for the use forms. The active compound can be applied to above-ground parts of plants, or via the soil. Treatment of seed is also possible.

When used against hygiene and stored-product pests, the active compound has an excellent residual action on wood and clay and a good stability to alkali on limed substrates.

Having favourable toxicity to warm-blooded species, the active compound is suitable for controlling pathogenic endoparasites which occur in humans and in particular in animal keeping and animal breeding, in productive animals, breeding animals, zoo animals, laboratory animals, animals for experimentation and pets. They are active against all or individual stages of development of the pests and against resistant and normally sensitive species. By controlling the pathogenic endoparasites the intention is to reduce disease, mortality and reductions in yield (for example in the production of meat, milk, wool, hides, eggs, honey, etc.), so that the use of the active compounds enables more economical and simpler animal keeping. The pathogenic endoparasites include cestodes, trematodes, nematodes and Acantocephalea, in particular:

From the order of the Pseudophyllidea, e.g.: Diphyllobothrium spp., Spirometra spp., Schistocephalus spp., Ligula spp., Bothridium spp., Diphlogonoporus spp.

From the order of the Cyclophyllidea, e.g.: Mesocestoides spp., Anoplocephala spp., Paranoplocephala spp., Moniezia spp., Thysanosomasa spp., Thysaniezia spp., Avitellina spp., Stilesia spp., Cittotaenia spp., Andyra spp., Bertiella spp., Taenia spp., Echinococcus spp., Hydatigera spp., Davainea spp., Raillietina spp., Hymenolepis spp., Echinolepis spp., Diorchis spp., Dipylidium spp., Joyeuxiella spp., Diplopylidium spp.

From the subclass of the Monogenea, e.g.: Gyrodactylus spp., Dactylogyrus spp., Polystoma spp.

From the subclass of the Digenea, e.g.: Diplostomum spp., Posthodiplostomum spp., Schistomsoma spp., Trichobilharzia spp., Ornithobilharzia spp., Austrobilharzia spp., Gigantobilharzia spp., Leucochloridium spp., Brachylaima spp., Echinostoma spp., Echinoparyphium spp., Echinochasmus spp., Hypoderaeum spp., Fasciola spp., Fasciolides spp., Fasciolopsis spp., Cyclocoelum spp., Typhlocoelum spp., Paramphistomum spp., Calicophoron spp., Cotylophoron spp., Gigantocotyle spp., Fischoederius spp., Gastrothylacus spp., Notocotylus spp., Catatropis spp., Plagiochis spp., Prosthogonimus spp., Dicrocoelium spp., Eurytrema spp., Troglotrema spp., Paragomimus spp., Collyriclum spp., Nanophyetus spp., Opisthorchis spp., Clonorchis spp., Metorchis spp., Heterophyes spp., Metagonismus spp.

From the order of the Enoplida e.g.: Trichuris spp., Capillaria spp., Trichomosoides spp., Trichinella spp.

From the order of the Rhabditia e.g.: Micronema spp., Strongyloides spp.

From the order of the Strongylida e.g.: Stronylus spp., Triodontophorus spp., Oesophagodontus spp., Trichonema spp., Gyalocephalus spp., Cylindropharynx spp., Poteriostomum spp., Cyclococercus spp., Cylicostephanus spp., Oesophagostomum spp., Chabertia spp., Stephanurus spp., Ancylostoma spp., Uncinaria spp., Bunostomum spp., Globocephalus spp., Syngamus spp., Cyathostoma spp., Metastrongylus spp., Dictyocaulus spp., Muellerius spp., Protostrongylus spp., Neostrongylus spp., Cystocaulus spp., Pneumostrongylus spp., Spicocaulus spp., Elaphostrongylus spp., Parelaphostrongylus spp., Crenosoma spp., Paracrenosoma spp., Angiostrongylus spp., Aelurostrongylus spp., Filaroides spp., Parafilaroides spp., Trichostrongylus spp., Haemonchus spp., Ostertagia spp., Marshallagia spp., Cooperia spp., Nematodirus spp., Hyostrongylus spp., Obeliscoides spp., Amidostomum spp., Ollulanus spp.

From the order of the Oxyurida e.g.: Oxyuris spp., Enterobius spp., Passalurus spp., Syphacia spp., Aspiculuris spp., Heterakis spp.

From the order of the Ascaridia e.g.: Ascaris spp., Toxascaris spp., Toxocara spp., Parascaris spp., Anisakis spp., Ascaridia spp.

From the order of the Spirurida e.g.: Gnathostoma spp., Physaloptera spp., Thelazia spp., Gongylonema spp., Habronema spp., Parabronema spp., Draschia spp., Dracunculus spp.

From the order of the Filariida e.g.: Stephanofilaria spp., Parafilaria spp., Setaria spp., Loa spp., Dirofilaria spp., Litomosoides spp., Brugia spp., Wuchereria spp., Onchocerca spp.

From the order of Gigantorhynchida e.g.: Filicollis spp., Moniliformis spp., Macracanthorhynchus spp., Prosthenorchis spp.

The productive and breeding animals include mammals such as cattle, horses, sheep, pigs, goats, camels, water buffalo, donkeys, rabbits, fallow deer and reindeer, furbearing animals such as mink, chinchilla and raccoon, birds such as chicken, geese, turkeys and ducks, fresh- and salt-water fish such as trout, carp and eels, reptiles, insects such as honey-bee and silkworm.

Laboratory and experimental animals include mice, rats, guinea-pigs, golden hamsters, dogs and cats.

The pets include dogs and cats.

Administration can be carried out both prophylactically and therapeutically.

Administration of the active compound is carried out directly or in the form of suitable preparations, enterally, parenterally, dermally, nasally, by treating the habitat or with the aid of active compound-containing shaped articles such as, for example, stripes, plates, bands, collars, ear-tags, straps for limbs, marking devices.

Enteral administration of the active compound is carried out, for example, orally in the form of powders, tablets, capsules, pastes, drinks, granules, orally administrable solutions, suspensions and emulsions, boluses, medicated feed or drinking water. Dermal administration is carried out, for example, in the form of dipping, spraying or pouring-on and spotting-on. Parenteral administration is carried out, for example, in the form of injections (intramuscular, subcutaneous, intravenous, intraperitoneal), or by implants.

Suitable preparations are:

solutions such as solutions for injection, oral solutions, concentrates for oral administration after dilution, solutions for use on the skin or in body cavities, pouring-on formulations, gels;

emulsions and suspensions for oral or dermal administration and for injection; semi-solid preparations;

formulations in which the active compound is processed in an ointment base or in an oil-in-water or water-in-oil emulsion base;

solid preparations such as powders, premixes or concentrates, granules, pellets, tablets, boluses, capsules; aerosols and inhalants, active compound-containing shaped articles.

Solutions for injection are administered intravenously, intramuscularly, and subcutanueously.

Solutions for injection are prepared by dissolving the active compound in a suitable solvent and adding, if appropriate, additives such as solubilizers, acids, bases, buffer salts, antioxidants, preservatives. The solutions are filtered and filled under sterile conditions.

Solvents which may be mentioned are: physiologically tolerable solvents such as water, alcohols such as ethanol, butanol, benzyl alcohol, glycerol, propylene glycol, polyethylene glycols, N-methyl-pyrrolidone, and mixtures thereof.

The active compound can optionally also be dissolved in physiologically tolerable vegetable or synthetic oils which are suitable for injection.

Solubilizers which may be mentioned are: solvents which promote the dissolution of the active compound in the main solvent or prevent its precipitation. Examples are polyvinylpyrrolidone, polyoxyethylated castor oil, polyoxyethylated sorbitan ester.

Preservatives are: benzyl alcohol, trichlorobutanol, p-hydroxybenzoic acid esters, n-butanol.

Oral solutions are administered directly. Concentrates are administered orally after prior dilution to the use concentration. Oral solutions and concentrates are prepared as described above for the solutions for injection, sterile procedures not being necessary.

Solutions for use on the skin are trickled on, spread on, rubbed in, sprinkled on or sprayed on. These solutions are prepared as described above for the solutions for injection.

It may be advantageous to add thickeners during preparation. Thickeners are: inorganic thickeners such as bentonites, colloidal silicic acid, aluminium monostearate, organic thickeners such as cellulose derivatives, polyvinyl alcohols and their copolymers, acrylates and methacrylates.

Gels are applied to or spread on the skin or introduced into body cavities. Gels are prepared by treating solutions which have been prepared as described in the case of the injection solutions with sufficient thickener that a clear material having an ointment-like consistency results. The thickeners employed are the thickeners given above.

Pour-on formulations are poured or sprayed onto limited areas of the skin, the active compound penetrating the skin and acting systemically.

Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added.

Solvents which may be mentioned are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, aromatic and/or aliphatic hydrocarbons, vegetable or synthetic oils, DMF, dimethylacetamide, N-methylpyrrolidone and 2,2-dimethyl-4-oxy-methylene-1,3-dioxolane.

Colorants are all colorants permitted for use on animals and which can be dissolved or suspended.

Absorption-promoting substances are, for example, DMSO, spreading oils such as isopropyl myristate, dipropylene glycol pelargonate, silicone oils, fatty acid esters, triglycerides, fatty alcohols.

Antioxidants are sulfites or metabisulfites such as potassium metabisulfite, ascorbic acid, butylhydroxytoluene, butylhydroxyanisole, tocopherol.

Light stabilizers are, for example, novantisolic acid.

Adhesives are, for example, cellulose derivatives, starch derivatives, polyacrylates, natural polymers such as alginates, gelatin.

Emulsions can be administered orally, dermally or as injections.

Emulsions are either of the water-in-oil type or of the oil-in-water type.

They are prepared by dissolving the active compound either in the hydrophobic or in the hydrophilic phase and homogenizing this with the solvent of the other phase with the aid of suitable emulsifiers and, if appropriate, other auxiliaries such as colorants, bioabsorption-promoting substances, preservatives, antioxidants, light stabilizers, viscosity-enhancing substances.

Hydrophobic phases (oils) which may be mentioned are: liquid paraffins, silicone oils, natural vegetable oils such as sesame oil, almond oil, castor oil, synthetic triglycerides such as caprylic/capric biglyceride, triglyceride mixture with vegetable fatty acids of the chain length $C_{8-12}$ or other specially selected natural fatty acids, partial glyceride mixtures of saturated or unsaturated fatty acids possibly also containing hydroxyl groups, mono- and diglycerides of the $C_8/C_{10}$ fatty acids.

Fatty acid esters such as ethyl stearate, di-n-butyryl adipate, hexyl laurate, dipropylene glycol perlargonate, esters of a branched fatty acid of medium chain length with saturated fatty alcohols of chain length $C_{16}$–$C_{18}$, isopropyl myristate, isopropyl palmitate, caprylic/capric acid esters of saturated fatty alcohols of chain length $C_{12}$–$C_{18}$, isopropyl stearate, oleyl oleate, decyl oleate, ethyl oleate, ethyl lactate, waxy fatty acid esters such as synthetic duck coccygeal gland fat, dibutyl phthalate, diisopropyl adipate, ester mixtures related to the latter, inter alia.

Fatty alcohols such as isotridecyl alcohol, 2-octyldodecanol, cetylstearyl alcohol, oleyl alcohol.

Fatty acids such as oleic acid and its mixtures.

Hydrophilic phases which may be mentioned are:
water, alcohols such as propylene glycol, glycerol, sorbitol and its mixtures.

Emulsifiers which may be mentioned are: non-ionic surfactants, e.g. polyethoxylated castor oil, polyethoxylated sorbitan monooleate, sorbitan monostearate, glycerol monostearate, polyoxyethyl stearate, alkylphenol polyglycol ether;
ampholytic surfactants such as di-Na N-lauryl-β-iminodipropionate or lecithin;
anionic surfactants, such as Na lauryl sulphate, fatty alcohol ether sulphates, mono/dialkyl polyglycol ether orthophosphoric acid ester monoethanolamine salt.

Further auxiliaries which may be mentioned are: substances which enhance the viscosity and stabilize the emulsion, such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silicic acid or mixtures of the substances mentioned.

Suspensions can be administered orally, dermally or as injection. They are prepared by suspending the active compound in a suspending agent, if appropriate with addition of other auxiliaries such as wetting agents, colorants, bioabsorption-promoting substances, preservatives, antioxidants, light stabilizers.

Liquid excipients which may be mentioned are all homogeneous solvents and solvent mixtures.

Wetting agents (dispersants) which may be mentioned are the surfactants given above.

Other auxiliaries which may be mentioned are those given above.

Semi-solid preparations can be administered orally or dermally. They differ from the suspensions and emulsions described above only by their higher viscosity.

For the production of solid preparations, the active compound is mixed with suitable excipients, if appropriate with addition of auxiliaries, and brought into the desired form.

Excipients which may be mentioned are all physiologically tolerable solid inert substances. Those used are inorganic and organic substances. Inorganic substances are, for example, sodium chloride, carbonates such as calcium carbonate, hydrogencarbonates, aluminium oxides, silicic acids, argillaceous earths, precipitated or colloidal silica, phosphates.

Organic substances are, for example, sugar, cellulose, foodstuffs and feeds such as milk powder, animal meal, grain meals and shreds, starches.

Auxiliaries are preservatives, antioxidants, colorants which have already been mentioned above.

Other suitable auxiliaries are lubricants and glidants such as magnesium stearate, stearic acid, talc, bentonites, disintegration-promoting substances such as starch or crosslinked polyvinylpyrrolidone, binders such as starch, gelatin or linear polyvinylpyrrolidone, and dry binders such as microcrystalline cellulose.

The active compounds can also be present in the preparations as a mixture with synergists or with other active compounds which act against pathogenic endoparasites. Such active compounds are, for example, L-2,3,5,6-tetrahydro-6-phenylimidazothiazole, benzimidazole carbamates, praziquantel, pyrantel, epsiprantel.

Ready-to-use preparations contain the active compound in concentrations of 10 ppm–20 per cent by weight, preferably of 0.1–10 per cent by weight.

Preparations which are diluted before use contain the active compound in concentrations of 0.5–90% by weight, preferably of 5–50% by weight.

In general, it has proven to be advantageous to administer amounts of about 1 to about 100 mg of active compound per kg of body weight per day to obtain effective results.

The preparation of the novel omphalotin and its biological properties are illustrated by the following examples.

In the examples (as in the rest of the description) percentages refer to percentages by weight and specifications of solvent mixtures refer to parts by volume, unless stated otherwise.

The test methods given in the examples are also particularly suitable to determine the omphalotin-containing fractions in the production of omphalotin. They can also be employed to estimate the particular omphalotin content.

EXAMPLE 1

Preparation of Omphalotin by Fermentation of Omphalotus Olearius No. 90 170 =DSM 9742

1.1 Preparation of solid media agar plates for the cultivation of Omphalotus olearius
1.2 Cultivation of Omphalotus olearius on solid media agar plates
1.3 Preparation of the culture medium for the precultivation of Omphalotus olearius
1.4 Inoculation and cultivation of Omphalotus olearius in the preculture medium
1.5 Preparation of the culture medium for the fermentation of Omphalotus olearius in the prefermenter
1.6 Inoculation and cultivation of Omphalotus olearius in the prefermenter
1.7 Preparation of the culture medium for the fermentation of Omphalotus olearius in the main fermenter
1.8 Inoculation and cultivation of Omphalotus olearius in the main fermenter
1.9 Harvest of the biomass after the fermentation
1.1 Preparation of solid media agar plates for the cultivation of Omphalotus olearius
For the preparation of solid media agar plates 4 g/l of glucose
4 g/l of yeast extract (Merck No. 3753, 64271 Darmstadt, Germany)
10 g/l of Löflund's barley malt extract
  (Dr. Fränkle & Max Eck, 70736 Fellbach, Germany)
20 g/l of agar agar (Merck No. 1615, 64271 Darmstadt, Germany)

are weighed in, dissolved in demineralized water and adjusted to pH 5.5 by addition of acid (c(HCl)=2 mol/l). A 2 l Erlenmeyer flask is charged with 1 l of the abovementioned solution, sealed with a cotton plug and sterilized in an autoclave (MMM, type LSS 666-1) at a temperature of 121° C. for 30 minutes.

With continuous stirring, the solution is cooled to a temperature of about 50 to 60° C. 20 ml of the solution are transferred into 90 mm Petri dishes under sterile conditions. After the solution has cooled, the filled Petri dishes can be stirred at room temperature for a maximum of 8 weeks prior to an inoculation.

1.2 Cultivation of Omphalotus olearius on solid media agar plates

The agar of a solid media agar plate which is densely colonized by Omphalotus olearius (in the present example No. 90 170) is divided under sterile conditions into pieces of a size of 1×1 cm with the aid of a scalpel. In each case one agar mycel piece is transferred with a pair of tweezers onto a solid media agar plate as described under 1.1 (mycel facing upwards) and incubated in an incubation cabinet (Heraeus, type BK 5060 E) at 27° C. in the dark for a maximum of 3 weeks. After 3 weeks have expired, the colonized plates can be used as inoculation plates for the fermentation, or they can be used once more for the inoculation of solid media agar plates.

1.3 Preparation of the culture medium for the precultivation of Omphalotus olearius 4 g/l of glucose
4 g/l of yeast extract (Merck No. 3753, 64271 Darmstadt, Germany)
10 g/l of Löflund's barley malt extract (Dr. Fränkle & Max Eck, 70736 Fellbach, Germany)

are weighed in, dissolved in demineralized water and adjusted to pH 5.5 by addition of acid (c(HCl)=2 mol/l). A 1 l Erlenmeyer flask is charged with 300 ml of the abovementioned solution, sealed with a cotton plug and autoclaved at 121° C. for 30 minutes. After cooling, the filled Erlenmeyer flasks are stored at room temperature for a maximum of 8 weeks prior to an inoculation.

1.4 Inoculation and cultivation of Omphalotus olearius in the preculture medium

In each case 300 ml of the culture medium described under 1.3 are inoculated with half of a densely populated 2- to 3-week-old solid media plate. To this end, 2- to 3-week-old solid media plates are divided under sterile conditions using a scalpel and transferred into a Waring mixer attachment (Waring Blender, type 32BL79) by means of a pair of tweezers. The solid media plates are mixed with 50 ml of sterile distilled water per solid media plate and homogenized for 30 seconds (15 seconds on low setting, 15 seconds on high setting). The total volume of the homogenized liquid is distributed evenly, using a 10 ml pipette (Becton Dickinson and Company, type Falcon), over the Erlenmeyer flask which had been prepared for inoculation. The incubation of the preculture flasks is carried out in a shaking cabinet (Braun Melsungen type BS 4) at a temperature of 27° C. and a shaking speed of 120 rpm for 5 days.

1.5 Preparation of the culture medium for the fermentation of Omphalotus olearius in the prefermenter A 42 l prefermenter (Braun Melsungen type Biostat P) is filled with 30 l of demineralized water, and 4 g/l   of glucose
4 g/l   of yeast extract (Merck No. 3753, 64271 Darmstadt, Germany)
10 g/l  of Löflund's barley malt extract (Dr. Fränkle & Max Eck, 70736 Fellbach, Germany)
0.25 g/l of anti-foam agent (Bayer, Baysilone E, 51371 Leverkusen, Germany)

are added. After filling, the fermenter is closed and the content is sterilized at a temperature of 121° C. for 30 minutes. After cooling to an operating temperature of 27° C., an overpressure of 0.3 bar is applied and the aeration rate is set to 0.25 vvm. After the oxygen saturation has reached the maximum, the $pO_2$ meter is calibrated to an initial value of 99%.

The pH of the medium is adjusted to 5.5 with the aid of acid (c(HCl)=2 mol/l).

1.6 Inoculation and cultivation of Omphalotus olearius in the prefermenter

The prefermenter is inoculated with 600 ml of the preculture prepared under 1.4. To this end, two 1 l Erlenmeyer flasks, each containing 300 ml of preculture, are transferred under sterile conditions into a 2 l glass bottle (Schott) (the bottle is connected to a Braun Melsungen inoculating apparatus via a silicone tube).

By means of this inoculating apparatus, the prefermenter is inoculated with the preculture under sterile conditions through a membrane in the lid.

Fermentation conditions:

| | |
|---|---|
| Temperature | 27° C. |
| Stirrer speed | 200 rpm |
| Aeration rate | 0.25 vvm |
| Pressure | 0.3 bar |
| pH | not controlled |
| Antifoam | as required |
| Incubation time | about 120 h, or at the most up to the point where the glucose concentration has decreased to c(glucose) ≦ 1 g/l. |

1.7 Preparation of the culture medium for the fermentation of Omphalotus olearius in the main fermenter A 450 l fermenter (Braun Melsungen type Biostat 450 D) is filled with 320 l of demineralized water, and

| | |
|---|---|
| 4 g/l | of glucose |
| 4 g/l | of Fermtech yeast extract (Merck No. 11926, 64271 Darmstadt, Germany) |
| 10 g/l | of Löflunds barley malt extract (Dr. Fränkle & Max Eck, 70736 Fellbach, Germany) |
| 0.25 g/l | of anti-foam agent (Bayer, Baysilone E, 51371 Leverkusen, Germany) | are added, based on the operating volume of 350 l. After filling, the fermenter is closed and the content is sterilized at a temperature of 121° C. for 30 minutes. After cooling to an operating temperature of 27° C., an overpressure of 0.3 bar is applied and the aeration rate is set to 0.25 vvm. After the oxygen saturation has reached the maximum, the $pO_2$ meter is calibrated to an initial value of 99%.

The pH of the medium is adjusted to 5.5 with the aid of acid (c(HCl)=2 mol/l).

1.8 Inoculation and cultivation of Omphalotus olearius in the main fermenter

After the glucose concentration c(glucose) in the culture filtrate of the prefermenter (see 1.6) has dropped to below ≦1 g/l, the main fermenter is inoculated with the content of the prefermenter via sterile transfer tubing. The glucose concentration is determined using a Beckmann glucose analyser.

Fermentation conditions:

| | |
|---|---|
| Temperature | 27° C. |
| Stirrer speed | 150 rpm |

-continued

Fermentation conditions:

| | |
|---|---|
| Aeration rate | 0.25 vvm |
| Pressure | 0.3 bar |
| pH | not controlled |
| Antifoam | as required |
| Incubation time | 72 h to 96 h |

1.9 Harvest of the biomass after the fermentation

At a glucose concentration of c(glucose) ≦1 g/l, the fermentation in the 450 l fermenter is terminated and the biomass is harvested. The content of the main fermenter is separated from the culture medium through gauze (Holthaus Medical, Verbandmull, Remscheid 11, Germany). The biomass filtercake is washed repeatedly with demineralized water and subsequently centrifuged in a tumble drier (Miele, type MZ 5942, Germany) at 4000 rpm for 3 minutes. 3 to 6 kg of moist biomass are harvested. The Omphalotus olearius biomass obtained is frozen at a temperature of −34° C. and stored until further work-up.

The fermentation of the other Omphalotus strains can be carried out similarly to the example above.

EXAMPLE 2

Isolation and Purification of Omphalotin 2.1 Preparation of the crude extract of the active compound from Omphalotus olearius and enrichment by liquid-liquid distribution (countercurrent distribution)

About 7 kg of mycel pellets (biomass) from the mycel obtained by Example 1 were homogenized a little at a time and digested twice with 20 l of acetone each time. The mixture was subsequently concentrated under reduced pressure using a rotary evaporator. 3 l of water and 3 l of ethyl acetate were added to the residue, which was then stirred. The upper phase was separated off and the solvent was distilled off under reduced pressure using a rotary evaporator, the lower phase was discarded. The distillation residue was taken up twice in 2 l of acetonitrile and 0.5 l of n-heptane each time. The mixtures were shaken and allowed to stand, and the lower phases that had formed were evaporated at about 40° C. The residue that remained was used for the countercurrent distribution, which was carried out as described below.

Parameters for the countercurrent distribution:

| | |
|---|---|
| Apparatus: | 25 ml apparatus (Labortec, Bubendorf, Switzerland) |
| Number of distribution elements: | 200 |
| Distribution system: | ethyl acetate/n-heptane/DMF (dimethylformamide)/water (2.5/7.5/5/5 v/v) |
| Phase ratio: | 1:1 |
| Separation stages: | n = 198 |
| Charge: | 945 mg in two elements |
| Work-up: | After the end of the distribution cycle (n = 198), the content of every 10th element was removed, the solvents were distilled off under reduced pressure using a rotary evaporator, and the residue was weighed and then taken up in 10 ml of methanol and examined by analytical HPLC (see Example 2.4). The omphalotin was found in elements E 48–87. The content of the elements was removed and combined. 2 l of water were added, the mixture was shaken and the upper phase was separated off. The lower phase was extracted 3 times with |

-continued

| Parameters for the countercurrent distribution: |
| --- |
| 1 l of ethyl acetate p.a. each time. The combined upper phases were then extracted 4 times with 0.5 l of water each time, and the solvent was distilled off under reduced pressure using a rotary evaporator. The yield of the concentrated crude extract that remained was 135 mg. Further purification was carried out as in Example 2.3. |

2.2. Preparation of the crude extract of the active compound from Omphalotus olearius and enrichment of the active compound by the principle of gel filtration 400 g of lyophilized mycel were extracted with stirring with 10 l of methanol for 2 hours. The solvent was removed using a rotary evaporator, yielding 35 g of crude extract. This crude extract was divided into portions of 10 g.

10 g of crude extract were dissolved in 5 ml of methanol and chromatographed over a separation column (height: 62 cm, diameter: 5 cm) filled with Sephadex LH-20 (Pharmacia, Upsalla, Sweden), using methanol as mobile phase. The flow rate was adjusted so that 5.5 ml/min of eluate were obtained. The eluate was collected in 100 ml fractions. The fractions containing omphalotin were combined and evaporated using a rotary evaporator. The original 10 g yielded 2 g of enriched extract. The 2 g of enriched extract were divided into portions of 200 mg.

200 mg of the abovementioned enriched extract were dissolved in 1 ml of methanol and applied to a second separation column (height 71.5 cm, diameter 2.5 cm, Sephadex LH-20). Chromatography was then carried out using a flow rate of 3 ml/min. The eluate was collected in 10 ml fractions. These fractions were likewise examined for omphalotin using analytical HPLC (see 2.4). Alternatively, the omphalotin could also be detected using a bioassay, for example as in Example B. The omphalotin-containing fractions were combined and evaporated using a rotary evaporator. The original 200 mg yielded 60 mg of further enriched extract. Further purification was carried out as in 2.3.

2.3 Final separation by preparative HPLC of the enriched active compound fractions obtained from the liquid-liquid distribution and the chromatographic separations Apparatus: Jasco PU-980 fitted with high pressure pump LG-980-02 gradient mixer and multiwavelength detector MD-910 (Gross-Umstadt, Germany)

Column: Hibar RT Lichrospher RP 18 WP 300® (particle diameter 12 μm),

Dimension: 250 mm column length*25 mm internal diameter

Eluent: A=water, B=acetonitrile

Flow rate: 5 ml/min

Detection: UV, λ=210 nm

Amount injected: 100 mg dissolved in 1 ml of acetonitrile

Gradients (all values in % by volume):

| Gradient 1: | | | Gradient 2: | | |
| --- | --- | --- | --- | --- | --- |
| 0 min | 100% A | 0% B | 0 min | 100% A | 0% B |
| 70 min | 70% A | 30% B | 40 min | 70% A | 30% B |
| 100 min | 40% A | 60% B | 100 min | 40% A | 60% B |
| 160 min | 0% A | 100% A | 160 min | 0% A | 100% B |
| 200 min | 0% A | 100% A | 200 min | 0% A | 100% B |
| 220 min | 100% A | 0% A | 220 min | 100% A | 0% B |

The samples from work-up 2.2 or 2.3 were initially chromatographed using gradient 1. To this end, 100 mg of the test substance were applied to the column in 1 ml of acetonitrile and chromatographed. The substantially pure active compound (omphalotin) eluted between 100 and 160 min at 30% of A. This fraction (=further purified product) was subsequently rechromatographed using gradient 2. The pure active compound was in the fraction which appeared between 100 and 160 min at 30% of B. The fraction containing pure active compound was freed from the solvent by distillation under reduced pressure using a rotary evaporator. Starting from 400 g of mycel, 11.5 mg of the pure active compound were obtained after the abovementioned steps had been carried out repeatedly.

2.4 Analytical high pressure liquid chromatography (HPLC)

Apparatus: HPLC 1090 having a diode array detector, Hewlett Packard (Waldbronn, Germany)

Column: Lichrocart, Lichrospher RP 18 WP 300® (particle diameter 5 μm)

Column dimension: 250*4 mm

Eluent: A=water, B=acetonitrile

Flow rate: 1 ml/min

Temperature: 40° C.

Detection: UV, λ=210 nm

Amount injected: 10 μl of a 0.1% strength solution (per cent by weight) of the sample in acetonitrile Gradient:

| Gradient | | |
| --- | --- | --- |
| 0 min | 0% B | 100% A |
| 15 min | 60% B | 30% A |
| 30 min | 100% B | 0% A |
| 35 min | 100% B | 0% A |
| 40 min | 0% B | 100% A |

Retention time for omphalotin under these conditions 20.8 min.

The fractions to be analysed were evaporated using a rotary evaporator, and then taken up in acetonitrile and injected onto the column as a 0.1% solution. The retention time for omphalotin was 20.8 min. Detection was by the UV spectrum which is automatically determined by the apparatus for the eluate.

Example A

Effect of omphalotin on *Heterodera schachtii*

Test nematode: *Heterodera schachtii*

Test method: The test substance is dissolved in methanol and pipetted into the wells of tissue culture plates (24 well tray). The methanol is then allowed to evaporate completely. Each well is filled with 0.8 ml of physiological sodium chloride solution. Subsequently, 0.2 ml of a nematode suspension (500 nematodes/ml) are pipetted into each well.

After 24 hours of incubation at room temperature and gentle shaking of the plates, the number of live and dead nematodes is counted.

The efficacy of the test substance is 100% if all test nematodes have been killed, and it is 0% if the number of nematodes that are still alive is the same as in the control.

The following efficacies were found:

| Omphalotin concentration (ppm = mg/l) | Efficacy (in % Abbott) |
|---|---|
| 10 ppm | 60 |
| 5 ppm | 40 |

Example B

Effect of omphalotin on *Meloidogyne incognita*

Test nematode: *Meloidogyne incognita*

Test method: The test substance is dissolved in methanol, pipetted into a 24 well microtitre plate, and the solvent is evaporated. Subsequently, 400 µl of nematode suspension are added into each well of the microtitre plate. When using Meloidogyne incognita, the number of nematodes is 100 L2/400 µl. To enhance the solubility of the samples in aqueous medium, the plate is shaken at 100 rpm (IKA MTS 4 plate shaker) for 15 minutes, and the first microscopic control (Leitz inverse microscope) is carried out subsequently. Evaluation is carried out after 16 h.

| | Nematicidal activity of omphalotin (µg/ml) | |
|---|---|---|
| Nematode | LD 90 | LD 50 |
| Meloidogyne incognita | 1–1.5 | 0.75 |

This test method is also particularly suitable for testing the active compound content of omphalotin-containing fractions in the preparation of omphalotin.

Example C

Effect of omphalotin on *Meloidogyne incognita* in a greenhouse (test plant: lettuce)

Test nematode: *Meloidogyne incognita*

Test method: The test substance, as a solution (10 ml per 250 ml of soil), is stirred homogeneously into a soil/leaf mould mixture, together with about 700 nematodes (mixture of eggs and larvae). The treated and inoculated soil substrate is filled into pots of a size of 7×7×6 cm into which lettuce (variety Attraktion) is sown. The seeds are pressed into the soil and covered with a thin layer of quartz sand. The pots are incubated in a greenhouse at 25° C. and kept uniformly moist. After 24 days, evaluation is carried out by washing the roots and determining the number of galls formed per plant.

The efficacy of the test substance is 100% if no galls have been formed, and it is 0% if the same number of galls has been formed as in the control.

| Test substance (concentration based on the volume of soil in ppm = mg/l) | Efficacy (in % Abbott) |
|---|---|
| Omphalotin 0.5 ppm | 48 |
| Omphalotin 2.5 ppm | 96 |

Example D

Effect of omphalotin on *Meloidogyne incognita* in a greenhouse (test plant: cucumbers)

Test nematode: *Meloidogyne incognita*

Test method: Two cucumber plants (variety Bella) each are grown in a soil/leaf mould mixture in pots of a size of 7×7×6 cm. The test substance is dissolved in methanol, and then diluted with water and put onto the 14day-old cucumber plants. Per pot, 10 ml of solution are used. 3 hours after the treatment, about 500 nematodes as a suspension are pipetted onto each pot. The pots are incubated in a greenhouse at a day temperature of 28° C. and a night temperature of 20° C. Evaluation is carried out after 20 days by washing the roots and determining the number of galls formed per plant.

The efficacy of the test substance is 100% if no galls have been formed, and it is 0% if the same number of galls has been formed as in the control.

| Test substance (concentration based on the volume of soil in ppm = mg/l) | Efficacy (in % Abbott) |
|---|---|
| Control methanol | 0 |
| Omphalotin 5 ppm | 61 |

Example E

Effect of the substance according to the invention on nematodes

Test nematode: *Radophulus similis*

Test Method

The substance is dissolved in methanol. Dilutions are then prepared and pipetted into the wells of a multiwell tissue culture plate (24 well). The methanol is then allowed to evaporate in a fume cupboard, and 0.8 ml of physiological sodium chloride solution is filled into the wells. 100 nematodes in 0.2 ml of water are added in each case by means of a pipette.

After 24 hours of incubation at about 22° C., evaluation is carried out under the microscope by determining the proportion of dead nematodes in the treated samples in comparison to the untreated control.

The efficacy of the test substance is 100% if all the nematodes have been killed. If the same number of nematodes are alive as in the control sample, the efficacy is 0%.

The following efficacies were found:

| Concentration of the substance according to the invention (ppm = mg/l) | Efficacy in % (according to Abbott) |
|---|---|
| 1 ppm | 23 |
| 10 ppm | 46 |
| 30 ppm | 54 |

Example F

Effect of the substance according to the invention on nematodes

Test nematode: *Pratylenchus penetrans*

Test Method

The substance is dissolved in methanol. Dilutions are then prepared and pipetted into the wells of a multiwell tissue culture plate (24 well). The methanol is then allowed to evaporate in a fume cupboard, and 0.8 ml of physiological sodium chloride solution is filled into the wells. 100 nematodes in 0.2 ml of water are added in each case by means of a pipette.

After 24 hours of incubation at about 22° C., evaluation is carried out under the microscope by determining the proportion of dead nematodes in the treated samples in comparison to the untreated control.

The efficacy is 100% if all the nematodes have been killed. If the same number of nematodes are alive as in the control sample, the efficacy is 0%.

The following efficacies were found:

| Concentration of the substance according to the invention (ppm = mg/l) | Efficacy in % (according to Abbott) |
|---|---|
| 10 ppm | 67 |
| 30 ppm | 97 |

Example G

Effect of omphalotin on insects

Test insect: *Plutella xylosella*

Test Method:

The test substance is dissolved in methanol and diluted to the test concentration using emulsifier-containing water (0.4 ml of emulsifier W/l of $H_2O$). With the aid of a cork borer, discs of a diameter of 4.4 cm are punched from cabbage leaves. The leaf discs are dipped into the solutions of the test substances by means of a pair of tweezers and subsequently placed in Petri dishes (diameter 9 cm) lined with filter paper (1 leaf disc/Petri dish). Each leaf disc is infected with 6 L3 larvae. Visual scoring is carried out after two, six and 16 days. On the third and, if appropriate, on the sixth day of the treatment, the food is replenished with untreated leaf discs.

The efficacy of the test substance is 100% if all test insects have been killed, and it is 0% if the same number of insects are still alive as in the control.

The following efficacies were found:

| Omphalotin concentration (ppm = mg/l) | Efficacy (in % Abbott) after 2 days | Efficacy (in % Abbott) after 6 days |
|---|---|---|
| 100 ppm | 33 | 100 |

Example H

Effect of omphalotin on various fungi and bacteria

Test method: Petri dishes are prepared using 10 ml of potato dextrose agar. The test substance is applied as a solution to the agar and spread with the spatula until the solution has been soaked up by the culture medium. The inoculum of the microorganisms to be tested, as spores or mycel fragments, is stamped onto the agar plates by pressing a stamp, which is, if appropriate, covered with felt, first onto a densely overgrown plate and then onto the test plate. After 5 to 6 days, the radial growth of the microorganism colonies is measured and compared to that of the untreated control.

The efficacy of the test substance is 100% if no growth is detected, and it is 0% if growth is identical to that of the control.

| Microorganism | Efficacy of omphalotin (10 ppm (= mg/l) based on the volume of the culture medium) |
|---|---|
| *Fusarium culmorum* | 51 |
| *Pythium ultimum* | 25 |
| *Fusarium graminearum* | 23 |
| *Alternaria mali* | 70 |
| *Rhizoctonia solani* | 90 |
| *Septoria nodorum* | 60 |
| *Phytophthora cactorum* | 50 |
| *Pseudocercosporella herpotrichoides* | 55 |
| *Pyricularia oryzae* | 70 |
| *Xanthomonas versicatoria* | 95 |

This test method can also be used in a particularly advantageous manner in the preparation of omphalotin to determine the omphalotin-containing fractions.

---

What is claimed is:

1. An isolated organochemical compound of the formula (I)

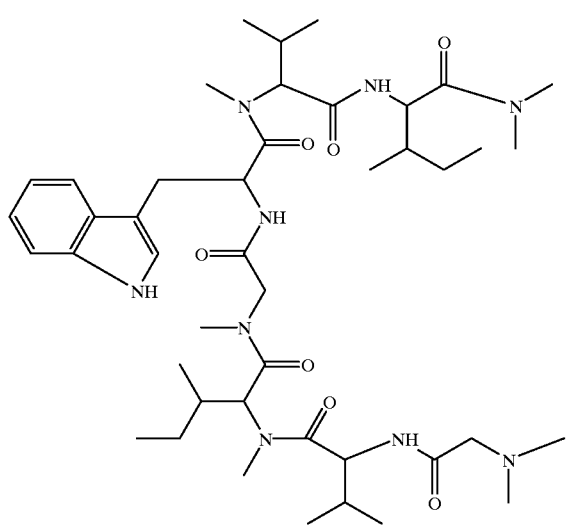

where —(terminal) represents —CH₃,

represents

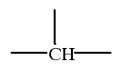

or (terminal) represents

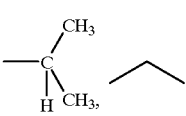

represents —CH$_2$—, represents

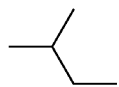

represents

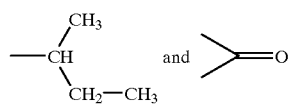

represents

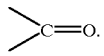

2. The isolated organochemical compound which is formed during the fermentation of Omphalotus olearius strains and which has the physico-chemical data and parameters shown in FIGS. 1, 2 and 3.

3. The process for preparing the isolated organochemical compound according to claim 1, wherein suitable microorganisms of the genera Omphalotus and Lampteromyces are cultivated under aerobic conditions in a culture medium which contains assimilable carbon and nitrogen sources and mineral salts, and the desired compound is isolated.

4. The process according to claim 3, wherein the Omphalotus olearius strains No. 83 039, 90 173 9738), 91 050, 92 095, 93 162 or 90 170 are employed.

5. A pesticidal composition comprising a pesticidally effective amount of a compound according to claim 1 and an extender.

6. A method of combating unwanted pests which comprises administering to such pests or to a locus from which it is desired to exclude such pests a pesticidally effective amount of a compound according to claim 1.

7. A pesticidal composition comprising a pesticidally effective amount of a compound according to claim 2 and an extender.

8. A method of combating unwanted pests which comprises administering to such pests or to a locus from which it is desired to exclude such pests a pesticidally effective amount of a compound according to claim 2.

* * * * *